US012559804B2

(12) United States Patent
Bonilla et al.

(10) Patent No.: US 12,559,804 B2
(45) Date of Patent: Feb. 24, 2026

(54) LOOP-MEDIATED ISOTHERMAL AMPLIFICATION PRIMERS FOR VIBRIO PARAHAEMOLYTICUS DETECTION AND USES THEREOF

(71) Applicant: NEOGEN FOOD SAFETY US HOLDCO CORPORATION, Lansing, MI (US)

(72) Inventors: Tonya D. Bonilla, Woodbury, MN (US); Neil Percy, St. Paul, MN (US); Christina A. Barnes, North Hudson, WI (US)

(73) Assignee: NEOGEN FOOD SAFETY US HOLDCO CORPORATION, Lansing, MI (US)

( * ) Notice: Subject to any disclaimer, the term of this patent is extended or adjusted under 35 U.S.C. 154(b) by 828 days.

(21) Appl. No.: 17/760,308

(22) PCT Filed: Feb. 16, 2021

(86) PCT No.: PCT/IB2021/051293
§ 371 (c)(1),
(2) Date: Aug. 8, 2022

(87) PCT Pub. No.: WO2021/165828
PCT Pub. Date: Aug. 26, 2021

(65) Prior Publication Data

US 2023/0119314 A1    Apr. 20, 2023

Related U.S. Application Data

(60) Provisional application No. 62/977,586, filed on Feb. 17, 2020.

(51) Int. Cl.
*C12Q 1/68* (2018.01)
*C12Q 1/689* (2018.01)

(52) U.S. Cl.
CPC ..................................... *C12Q 1/689* (2013.01)

(58) Field of Classification Search
None
See application file for complete search history.

(56) References Cited

PUBLICATIONS

NEB catalog (1996/1997), pp. 111 (Year: 1997).*
Froussard (PCR Methods and Applications, 1993, 2: 185-190) (Year: 1993).*

* cited by examiner

*Primary Examiner* — Juliet C Switzer
(74) *Attorney, Agent, or Firm* — HYLTON-RODIC LAW PLLC

(57) ABSTRACT

Primers and primer sets for amplification of *Vibrio parahaemolyticus* DNA and methods of detecting *Vibrio parahaemolyticus* using the primers and primer sets.

20 Claims, No Drawings

Specification includes a Sequence Listing.

1

LOOP-MEDIATED ISOTHERMAL AMPLIFICATION PRIMERS FOR VIBRIO PARAHAEMOLYTICUS DETECTION AND USES THEREOF

CROSS REFERENCE TO RELATED APPLICATIONS

This application is a national stage filing under 35 U.S.C. 371 of PCT/IB/2021/051293, filed 16 Feb. 2021, which claims the benefit of U.S. Provisional Application No. 62/977,586, filed 17 Feb. 2020, the disclosures of which are incorporated by reference in their entireties herein.

SEQUENCE LISTING

This application contains a Sequence listing electronically submitted via EFS-Web to the United States Patent and Trademark Office as an ASCII text file entitled "82721WO003_2_ST25.txt" having a size of 1.92 kilobytes and created on Feb. 4, 2022. The information contained in the Sequence Listing is incorporated by reference herein.

BACKGROUND

Some foodborne illnesses, such as vibriosis, are caused by *Vibrio parahaemolyticus*. Transmission of *V. parahaemolyticus* can occur through eating food, such as shellfish, that contains the microorganism.

Loop-mediated isothermal amplification (LAMP) is a method of amplifying DNA that has been described, for example, in WO0028082, WO0134790, and WO0177317. Detection of amplified DNA has been performed with the Molecular Detection Kit available from 3M Company (St. Paul, MN).

DETAILED DESCRIPTION

Throughout this disclosure, singular forms such as "a," "an," and "the" are often used for convenience; however, the singular forms are meant to include the plural unless the singular alone is explicitly specified or is clearly indicated by the context. When the singular alone is called for, the term "one and only one" is typically used.

Some terms in this disclosure are defined below. Other terms will be familiar to the person of skill in the art and should be afforded the meaning that a person of ordinary skill in the art would have ascribed to them.

The terms "common," "typical," and "usual," as well as "commonly," "typically," and "usually" are used herein to refer to features that are often employed in the invention and, unless specifically used with reference to the prior art, are not intended to mean that the features are present in the prior art, much less that those features are common, usual, or typical in the prior art.

The term "LAMP" is an acronym for loop-mediated isothermal amplification, a method of amplifying DNA that has been described, for example, in WO0028082, WO0134790, and WO0177317.

Detection of microorganisms can be accomplished by amplifying a segment of DNA that is specific to the type of microorganism to be detected followed by detection of the amplified DNA. If the DNA is present at detectable levels after amplification, this indicates the presence of the microorganism of interest. If no DNA is present, this indicates that the DNA of interest, and thus the microorganism of interest, was not present. PCR is one well-recognized way to amplify DNA that relies on thermocycling. LAMP is another method for amplifying DNA. Unlike PCR, LAMP takes place at a constant elevated temperature, typically about 60° C., such as 50° C. to 70° C., thus eliminating the need for thermocycling.

Briefly, LAMP requires four different primers, although frequently six primers are used. The required primers are two lamp primers and two displacement primers. The optional primers are two loop primers. The lamp primers have a 3' segment that binds to a specific target sequence and a 5' segment that is the reverse compliment to an internal target sequence. Extension from a displacement primer generates a primary amplicon and formation of a self-priming loop structure. The loop primers, which are optional, bind within the loop structures to facilitate exponential amplification. A primer set for amplification contains two lamp primers (known as LampF and LampB), two displacement primers (known as DisF and DisB), and optionally one or two loop primers (known as LoopF and LoopB).

Of the primers in each primer set, at least the two lamp primers do not exist in nature. This is because one end of each lamp primer is complementary to a segment of DNA on the forward strand of the template, and the other end of each lamp primer is complementary to a non-contiguous segment of DNA on the reverse strand of the template. Further, at least the 5' primer or primer segment of each lamp primer is a reverse complement of the target DNA, which also does not exist in nature.

Once amplified, the DNA can be detected by a variety of methods, including the bioluminescence in real time (BART) method. The 3M Molecular Detection System (available from 3M Company, St. Paul, MN, USA) is a commercially available system that uses BART to detect microorganisms after the portion of DNA of the microorganisms is amplified with LAMP.

A problem is that there are no known primers that can be used for LAMP amplification of a portion of *V. parahaemolyticus* nuclear DNA that are unique and specific so as to be useful to identify the *V. parahaemolyticus* microorganism. Particularly the problem can be stated as how to identify any of the various strains of the *V. parahaemolyticus* microorganism while not obtaining a false positive by mistaking another species of *Vibrio* microorganism for the *V. parahaemolyticus* microorganism. Another problem is that *V. parahaemolyticus* bacteria are not currently detectable by way of LAMP amplification followed by a detection method. More particularly, primers for rapid amplification and detection, such as times no more than 48 hours, no more than 24 hours, no more than 12 hours, no more than 6 hours, no more than 4 hours, no more than 2 hours, no more than 90 minutes, or even no more than 60 minutes, are not available.

Another problem is identifying a suitable gene for the specific detection of *V. parahaemolyticus* without detecting other *Vibrio* species. Another problem is finding a use of the VP175 gene, particularly for detection of *V. parahaemolyticus*. This gene is not known as a target for *V. parahaemolyticus* detection. A related problem is finding a LAMP primer set that detects targets on the VP175 gene of *V. parahaemolyticus*.

Briefly, as solution to one or more of these problems, and some other problems, this disclosure provides primers that are useable for amplification of *V. parahaemolyticus* by LAMP methodology. The primers may particularly detect the VP175 gene of *V. parahaemolyticus*.

A primer set for *V. parahaemolyticus* can include a Lamp primer, particularly the *V. parahaemolyticus* LampF primer having SEQ ID NO: 1. Optionally, the *V. parahaemolyticus* LampF primer can have a sequence that has at least 99% homology, at least 95% homology, at least 90% homology, at least 85% homology, or at least 80% homology to SEQ ID NO: 1

Any suitable displacement primer for *V. parahaemolyticus* can be used in the primer set along with the aforementioned LampF primer. One suitable displacement primer is the *V. parahaemolyticus* DisF primer having the sequence of SEQ ID NO: 2. Optionally, *V. parahaemolyticus* DisF primer can have a sequence that has at least 99% homology, at least 95% homology, at least 90% homology, at least 85% homology, or at least 80% homology to SEQ ID NO: 2. In principle other displacement primers could be used with the Lamp primer, such as the Lamp primer discussed above.

The disclosed primer set for *V. parahaemolyticus* can optionally include a suitable loop primer. One suitable loop primer is the *V. parahaemolyticus* LoopF primer having the sequence of SEQ ID NO: 2. Optionally, the *V. parahaemolyticus* LoopF primer can have a sequence that has at least 99% homology, at least 95% homology, at least 90% homology, at least 85% homology, or at least 80% homology to SEQ ID NO: 3. In principle, other loop primers could be used.

A primer set for *V. parahaemolyticus* can include, typically in addition to but in some cases as an alternative, to the *V. parahaemolyticus* LampF primer discussed above, the *V. parahaemolyticus* LampB primer having the sequence of SEQ ID NO: 4. Optionally, the *V. parahaemolyticus* LampB primer can have a sequence that has at least 99% homology, at least 95% homology, at least 90% homology, at least 85% homology, or at least 80% homology to SEQ ID NO: 4.

Any suitable displacement primer for *V. parahaemolyticus* can be used in the primer set along with one or both of the aforementioned lamp primers, that is, with the *V. parahaemolyticus* LampF primer, the *V. parahaemolyticus* LampB primer, or both the *V. parahaemolyticus* LampF primer and the *V. parahaemolyticus* LampB primer. One suitable displacement primer is the *V. parahaemolyticus* DisB primer having the sequence of SEQ ID NO: 5. Optionally, the *V. parahaemolyticus* DisB primer can have a sequence that has at least 99% homology, at least 95% homology, at least 90% homology, at least 85% homology, or at least 80% homology to SEQ ID NO: 5. In principle, other displacement primers could be used.

A primer set for *V. parahaemolyticus* can optionally include a suitable loop primer. One suitable loop primer is the stxl all var LoopB primer having the sequence of SEQ ID NO: 6. Optionally, the stxl all var LoopB primer can have a sequence that has at least 99% homology, at least 95% homology, at least 90% homology, at least 85% homology, or at least 80% homology to SEQ ID NO: 6. In principle, other loop primers could be used.

A summary of the primers and primer sets disclosed herein can be found in Table 1.

TABLE 1

| Primer | SEQ ID NO | Sequence | Comments |
|---|---|---|---|
| LampF | 1 | TCGCTATTACCTTG GCAACGCTTCTCAA CAAAGACATGAATG A | New chemical entity that does not occur in nature. Disclosed by itself and in combination with other primers. |

4

TABLE 1-continued

| Primer | SEQ ID NO | Sequence | Comments |
|---|---|---|---|
| LampB | 2 | GCTTCTAAGATGTG GAACATCTGCTTGG ATAATTGGCTATGC | New chemical entity that does not occur in nature. Disclosed by itself and in combination with other primers. |
| DisF | 3 | GATGTCCGTCAACA GCAC | May be used in a primer set with LampF, LampB, or both LampF and LampB. May optionally be used with DisB. May optionally be used with LoopF, LoopB, or both LoopF and LoopB. |
| DisB | 4 | ACTCAAAGCTTATC TCTTTGGT | May be used in a primer set with LampF, LampB, or both LampF and LampB. May optionally be used with DisF. May optionally be used with LoopF, LoopB, or both LoopF and LoopB. |
| LoopF | 5 | CCATGGCTCAAGAG TTCAT | Optional component of any primer set. |
| LoopB | 6 | GGCGACTGAACGAT TTAGG | Optional component of any primer set. |

Any primer set as described herein can be in the form of a lyophilized pellet or powder, which can optionally contain other materials. Examples of other materials that can be included in the lyophilized pellet or powder include sugars, such as glucose, lyophilization aids, preservatives, antioxidants, and the like.

In use, any of the aforementioned primer sets can be used in a method of amplifying target DNA. In such a method, the target DNA is exposed to any of the aforementioned primer sets of any of the preceding claims under conditions that are suitable for amplification of the target DNA. The target DNA is typically DNA of the *V. parahaemolyticus* organism, and particularly DNA from VP175 gene of the *V. parahaemolyticus*. While conditions that are suitable for amplification of target DNA with primers are known or readily determined by the skilled artisan, particular conditions that may be used include a temperature of 50° C. to 70° C.

The method can further comprise detecting the target DNA. Methods of detecting target DNA are known. One exemplary method entails the use of the 3M Molecular Detection System. Other methods may also be employed.

Examples

Bioinformatics and Primer Design

Available complete genomes from NCBI (National Center for Biotechnology Information) were compiled and whole genome alignments were performed using the progressiveMauve algorithm of Mauve genome aligner, one chromosome/replicon at a time. The alignments were manually scanned for orthologous genes with moderate to high level of conservation based on similarity plots generated by Mauve. Selected genes were searched against the NCBI nucleotide collection (nr/nt) using the BLAST (Basic Local Alignment Search Tool) algorithm for comparing primary biological sequence information. Percent nucleic acid identity was determined to the worst inclusive match and best inclusive match over 100% coverage. Multiple sequence alignments using Clustal W in BioEdit were generated for the highest scoring gene candidates. All available *Vibrio parahaemolyticus* sequences from the NCBI nr/nt and refseq genomic databases were included in the alignment Regions amenable for LAMP primer design were identified and further verified for specificity by BLAST analysis against the NCBI non-redundant (nr/nt) nucleotide database. A set of LAMP primers designed to detect the VP175 gene is shown in Table 2 (SEQ ID NO: 7-10).

TABLE 2

| Portion | Sequence |
| --- | --- |
| LampF 3' | CTTCTCAACAAAGACATGAATGA |
| LampF 5' | TCGCTATTACCTTGGCAAC |
| LampB 3' | GCTTGGATAATTGGCTATGC |
| LampB 5' | GCTTCTAAGATGTGGAACATCT |

Culture Method

The cultures identified in Table 3 were obtained from either the BEI Resources Repository (BEI) or the American Type Culture Center (ATCC) and were propagated by streaking a frozen culture onto a tryptic soy agar plate and incubating the plate for 24 hours at 32° C. Colonies were suspended into 10 mL of buffered peptone water (available as BPW-ISO from 3M Company, St. Paul, MN, US) broth with a 10 µL inoculation loop. Cultures were grown for 18 hours at 32° C. and were visibly turbid after incubation.

After incubation, cultures were diluted to $1\times10^{\wedge}6$ CFU/mL into BPW-ISO. 20 µL of each dilution was dispensed into lysis buffer (commercially available from 3M Company as part of the 3M™ Molecular Detection Assay 2—cronobacter kit.) Samples were heated to 100° C. for 15 minutes then colled for 5 minutes. 20 µL of each sample was then dispensed into 3M™ Molecular Detection Assay 2—cronobacter kit reagent tubes.

2 µL of a mixture of a 10× primer mix with 4 mM $MgSO_4$ (New England Biolobs, Ipswich, MA, US) was added to the reagent tube and mixed up and down five times with a multichannel pipette. In each tube, the final concentration of each LAMP primer was 0.8 µL; the final concentration of each LOOP primer was 0.4 µL; the final concentration of each DIS primer was 0.2 µL; and the final concentration of $MgSO_4$ was 0.4 mM.

Tests to determine the presence of each sample were performed using the 3M™ Molecular Detection System 2 instrument for 60 minutes at 60° C. The results are shown in Table 3, where a positive outcome means that the test indicated the presence of the organism and a negative outcome means that the test indicated the absence of the organism.

TABLE 3

| Example or Comparative Example | Organisms Designation | Organism | Source of Culture | Expected Outcome | Actual Outcome |
| --- | --- | --- | --- | --- | --- |
| Ex-1 | NR-21990 | *Vibrio parahaemolyticus* | BEI | Positive | Positive |
| Ex-2 | NR-21991 | *Vibrio parahaemolyticus* | BEI | Positive | Positive |
| Ex-3 | NR-21992 | *Vibrio parahaemolyticus* | BEI | Positive | Positive |
| Ex-4 | NR-21993 | *Vibrio parahaemolyticus* | BEI | Positive | Positive |
| Ex-5 | NR-22004 | *Vibrio parahaemolyticus* | BEI | Positive | Positive |
| Ex-6 | NR-22017 | *Vibrio parahaemolyticus* | BEI | Positive | Positive |
| Ex-7 | NR-22000 | *Vibrio parahaemolyticus* | BEI | Positive | Positive |
| CE-1 | ATCC 33815 | *Vibrio vulnificus* | BEI | Negative | Negative |
| Ex-8 | NR-22013 | *Vibrio parahaemolyticus* | BEI | Positive | Positive |
| Ex-9 | NR-22007 | *Vibrio parahaemolyticus* | BEI | Positive | Positive |
| CE-2 | ATCC 33816 | *Vibrio vulnificus* | ATCC | Negative | Negative |
| CE-3 | ATCC 33149 | *Vibrio vulnificus* | ATCC | Negative | Negative |
| Ex-10 | NR-22002 | *Vibrio parahaemolyticus* | BEI | Positive | Positive |
| CE-4 | NR-156 | *Vibrio cholerae* | BEI | Negative | Negative |
| CE-5 | NR-28825 | *Vibrio cholerae* | BEI Resources | Negative | Negative |
| CE-6 | NR-28824 | *Vibrio cholerae* | BEI | Negative | Negative |

What is claimed is:

1. A primer set comprising a primer having at least 90% homology over the full length to SEQ ID NO: 1, and optionally comprising a primer having at least 80% homology over the full length to SEQ ID NO: 4.

2. The primer set of claim 1, comprising a primer having at least 95% homology over the full length to SEQ ID NO: 1.

3. The primer set of claim 1, comprising a primer having SEQ ID NO: 1.

4. The primer set of claim 1, comprising a primer having at least 95% homology to SEQ ID NO: 4.

5. The primer set of claim 1, comprising a primer having SEQ ID NO: 4.

6. The primer set of claim 1, further comprising a primer having at least 80% homology to SEQ ID NO: 2.

7. The primer set of claim 1, comprising a primer having SEQ ID NO: 2.

8. The primer set of claim 1, further comprising a primer having least 80% homology to SEQ ID NO: 3.

9. The primer set of claim 1, comprising a primer having SEQ ID NO: 3.

10. The primer set of any of claim 1, further comprising a primer having least 80% homology to SEQ ID NO: 5.

11. The primer set of claim 1, comprising a primer having SEQ ID NO: 5.

12. The primer set of claim 1, further comprising a primer having at least 80% homology to SEQ ID NO: 6.

13. The primer set of claim 1, comprising a primer having SEQ ID NO: 6.

14. A lyophilized primer set comprising the primer set of claim 1.

15. A pellet comprising the lyophilized primer set of claim 14.

16. A method of amplifying target DNA comprising exposing the target DNA to the primer set of claim 1 under conditions that are suitable for amplification of the target DNA.

17. The method of claim 16, wherein the conditions include a temperature of 50° C. to 70° C.

18. The method of claim 16, further comprising detecting the presence of amplified target DNA.

19. The method of claim 16, wherein the target DNA is DNA of *V. parahaemolyticus.*

20. The method of claim 16, wherein the target DNA is DNA of the VP175 gene of *V. parahaemolyticus.*

* * * * *

SEQUENCE LISTING

<160> NUMBER OF SEQ ID NOS: 10

<210> SEQ ID NO 1
<211> LENGTH: 43
<212> TYPE: DNA
<213> ORGANISM: artificial
<220> FEATURE:
<223> OTHER INFORMATION: synthetic

<400> SEQUENCE: 1
tcgctattac cttggcaacg cttctcaaca aagacatgaa tga          43

```
<210> SEQ ID NO 2
<211> LENGTH: 42
<212> TYPE: DNA
<213> ORGANISM: artificial
<220> FEATURE:
<223> OTHER INFORMATION: synthetic

<400> SEQUENCE: 2
gcttctaaga tgtggaacat ctgcttggat aattggctat gc                   42

<210> SEQ ID NO 3
<211> LENGTH: 18
<212> TYPE: DNA
<213> ORGANISM: Vibrio parahaemolyticus

<400> SEQUENCE: 3
gatgtccgtc aacagcac                                              18

<210> SEQ ID NO 4
<211> LENGTH: 22
<212> TYPE: DNA
<213> ORGANISM: Vibrio parahaemolyticus

<400> SEQUENCE: 4
actcaaagct tatctctttg gt                                         22

<210> SEQ ID NO 5
<211> LENGTH: 19
<212> TYPE: DNA
<213> ORGANISM: Vibrio parahaemolyticus

<400> SEQUENCE: 5
ccatggctca agagttcat                                             19

<210> SEQ ID NO 6
<211> LENGTH: 19
<212> TYPE: DNA
<213> ORGANISM: Vibrio parahaemolyticus

<400> SEQUENCE: 6
ggcgactgaa cgatttagg                                             19

<210> SEQ ID NO 7
<211> LENGTH: 23
<212> TYPE: DNA
<213> ORGANISM: artificial
<220> FEATURE:
<223> OTHER INFORMATION: synthetic

<400> SEQUENCE: 7
cttctcaaca aagacatgaa tga                                        23

<210> SEQ ID NO 8
<211> LENGTH: 19
<212> TYPE: DNA
<213> ORGANISM: artificial
<220> FEATURE:
<223> OTHER INFORMATION: synthetic

<400> SEQUENCE: 8
tcgctattac cttggcaac                                             19

<210> SEQ ID NO 9
<211> LENGTH: 20
```

-continued

```
<212> TYPE: DNA
<213> ORGANISM: artificial
<220> FEATURE:
<223> OTHER INFORMATION: synthetic

<400> SEQUENCE: 9
gcttggataa ttggctatgc                                                      20

<210> SEQ ID NO 10
<211> LENGTH: 22
<212> TYPE: DNA
<213> ORGANISM: artificial
<220> FEATURE:
<223> OTHER INFORMATION: synthetic

<400> SEQUENCE: 10
gcttctaaga tgtggaacat ct                                                   22
```